United States Patent [19]

Chignac et al.

[11] 4,127,604
[45] Nov. 28, 1978

[54] PROCESS FOR THE PREPARATION OF ACETIC ACID DERIVATIVES

[75] Inventors: Michel Chignac, Sisteron; Claude Grain, Volonne; Charles Pigerol, Saint-Ouen, all of France

[73] Assignee: Labaz, Paris, France

[21] Appl. No.: 800,344

[22] Filed: May 25, 1977

[30] Foreign Application Priority Data

Mar. 15, 1977 [FR] France .................................. 77 07588

[51] Int. Cl.² ....................... C07C 51/06; C07C 51/52
[52] U.S. Cl. ................................. 562/606; 260/465.1; 260/465.4; 260/561 R
[58] Field of Search ................ 260/540, 561 R, 465.1, 260/465.4

[56] References Cited

FOREIGN PATENT DOCUMENTS 2,442 4/1964 France ..................................... 260/540

OTHER PUBLICATIONS

Sarel et al., J.A.C.S., 78, 5416-5420 (1956).
Tsai et al., J.A.C.S., 79, 2530 (1957).

Primary Examiner—Vivian Garner
Attorney, Agent, or Firm—Warren D. McPhee

[57] ABSTRACT

Process for the preparation of di-n-propyl acetic acid of formula:

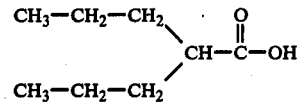

and its non-toxic alkali and alkaline earth metal salts whereby in a single stage, sodium n-propylate in n-propanol medium is added to a reaction medium formed of a cyanacetic ester of general formula:

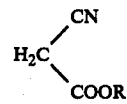

in which R represents an alkyl radical having from 1 to 4 carbon atoms, and n-propyl bromide or iodide, the alkylation reaction taking place under reflux, the crude ester obtained is saponified with a 10 to 20% solution of sodium or potassium hydroxide, the salt thus obtained is acidified with a strong acid, to give the crude di-n-propyl cyanacetic acid, which is decarboxylated by heating at a temperature between 140° and 190° C, to provide the di-n-propyl acetonitrile, the di-n-propyl acetonitrile obtained is hydrolysed by means of an aqueous solution of 75 to 80% sulphuric acid at a temperature of 80°–140° C to give the crude di-n-propyl acetamide, which is hydrolyzed by means of an aqueous solution of 75–80% sulphuric acid at a temperature of 40°–80° C in the presence of sodium nitrite, to provide di-n-propyl acetic acid, which is caused to react, if so desired, with an alkali metal hydroxide or alkaline earth metal oxide in order to obtain the corresponding salt.

16 Claims, No Drawings

PROCESS FOR THE PREPARATION OF ACETIC ACID DERIVATIVES

The present invention relates generally to a novel process for the preparation of derivatives of acetic acid and also to the derivatives obtained by this process.

The invention is more especially concerned with a novel process for the preparation of di-n-propyl acetic acid of the formula:

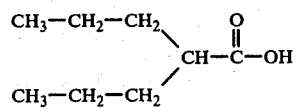

as well as its non-toxic alkali and alkaline earth metal salts such as its lithium, sodium, potassium, calcium and magnesium salts.

Di-n-propyl acetic acid and its alkali and alkaline earth metal salts are known products which have pharmacological properties, as disclosed in B.S.M. (French Special Medicament Patent) N° 2442 M. They have in particular neurotropic properties and more especially extremely valuable anticonvulsive properties.

At the present time, sodium di-n-propyl acetate, generally known as sodium valproate, constitutes one of the most remarkable and the most widely commercialised anti-epileptic agents. It is also used for the treatment of character or personality disorders associated with epilepsy.

One of the most conventional and the most widely used methods of preparing di-n-propyl acetic acid and its alkali metal salts consists in treating diethyl malonate, under pressure and in a methanolic medium, first with sodium methylate and then with allyl chloride, these two operations each being carried out according to two different methods of procedure.

The diethyl diallyl malonate is then saponified with sodium hydroxide and the salt which is formed is acidified to give diallyl malonic acid, which is decarboxylated by heating to diallyl acetic acid, which is itself subsequently hydrogenated on palladised carbon to di-n-propyl acetic acid.

This process is characterised by five stages, of which the first comprises two phases. Furthermore, the operating conditions which have to be respected cause difficulties of a technical nature, such as heating under pressure during the first stage and hydrogenation on a catalyst.

Moreover, secondary reactions may cause the formation of impurities, for example, 2-allyl valerolactone concurrently with diallyl malonic acid, which must be eliminated.

All these inconveniences have an unfavourable influence on the yield and the cost price of the final product.

Finding a process of preparing di-n-propyl acetic acid and its alkali and alkaline earth metal salts which obviates the disadvantages indicated above is therefore of paramount importance.

The synthesis of dialkyl acetic acids, from dialkyl acetonitriles, themselves obtained from cyanacetic esters, has been described in the literature in the particular case of certain dialkyl acetic acids. For example, the preparation of diisopropyl acetic acid by hydrolysis of diisopropyl acetonitrile has been described by SAREL and collaborators, in J. A. Chem. Soc. 78, 5416-5420 (1956) and by TSAI and collaborators in J. Am. Chem. Soc. 79, 2530 (1957).

These processes are characterised by a succession of five or six quite distinct stages, starting from an ester of cyanacetic acid namely:
— an alkylation phase for obtaining a diisopropyl cyanacetic ester,
— a phase for the elimination of the monoalkylated ester,
— a saponification phase of the diisopropyl cyanacetic ester,
— a decarboxylation phase of the diisopropyl cyanacetic acid which is obtained in order to provide the diisopropyl acetonitrile,
— a phase of sulphuric acid hydrolysis to the amide followed by hydrolysis to diisopropyl acetic acid with intermediate separation of the amide, in the case of the process of SAREL and collaborators, and without separation of the amide, in the case of the process of TSAI and collaborators.

Thus, SAREL and collaborators prepare diisopropyl acetic acid from a cyanacetic ester by treating an alcoholic solution of this ester with sodium and by causing this mixture to react for several hours with an excess of isopropyl iodide. The monoalkylated product is eliminated by means of a 10% sodium hydroxide solution and the crude dialkyl ester obtained in this way is then treated with a 35% potassium hydroxide solution for 16 hours. After acidification, the diisopropyl cyanacetic acid which is obtained is decarboxylated by distillation in the presence Chem. e its weight of molten potassium hydroxide [MARSHALL - J. Am. Soc., 2754-2761 (1930)]. The diisopropyl acetonitrile thus obtained is then hydrolysed in the presence of twice its weight of 96% sulphuric acid at 140°-155° C. for 75 minutes and the crude diisopropyl acetamide is then hydrolysed by twice its weight of 75% sulphuric acid for one hour at 80-85° C. in the presence of powdered sodium nitrite (4.15 mols of nitrite/mol of amide).

As regards TSAI and collaborators, these authors also prepare diisopropyl acetic acid from diisopropyl acetonitrile obtained by first reacting ethyl cyanaceate with isopropyl iodide under reflux for 3 hours in the presence of sodium ethylate in ethanolic medium then again adding sodium ethylate followed by isopropyl iodide and heating the reaction medium once again under reflux for 3 hours. After a further addition of sodium ethylate followed by isopropyl iodide, and again heating for 2 hours under reflux, the resulting diisopropylated derivative is washed with a 15% potassium hydroxide solution and thereafter hydrolysed by means of an alcoholic solution of 35% potassium hydroxide under reflux for 26 hours and the diisopropyl cyanacetic acid is heated at 180°-200° C. in the presence of copper powder [NEWMAN and collacorators, J. Am. Chem. Soc., 82, 873-875 (1960)]. the diisopropyl acetonitrile obtained is then hydrolysed with 75% sulphuric acid (1.7 g of acid/g of nitrile) for 30 minutes at 140° C. and the amide not isolated is treated with sodium nitrite (1.5 mol of nitrite/mol of nitrile) at a temperature of 50°-60° C. for one hour.

In view of the great similarity in chemical structure between diisopropyl acetic acid and di-n-propyl acetic acid, attempts have been made to apply to the preparation of this latter compound, the processes indicated above for the preparation of diisopropyl acetic acid.

Tests carried out using the procedure of SAREL and collaborators gave low yields of pure di-n-propyl acetic acid of the order of 20%, without separation of the intermediate di-n-propyl acetamide. When the intermediate amide is hydrolysed after separation, as proposed by SAREL and collaborators, the yields of di-n-propyl acetic acid are ridiculously low being less than 10%.

Likewise, by applying the procedure of TSAI and collaborators, only 38.5% of pure di-n-propyl acetic acid were obtained from the starting cyanacetic ester.

In conclusion, all the aforesaid methods, applied to the preparation of di-n-propyl acetic acid, are essentially characterized by their complexity and long duration by the impurities obtained at the different stages, necessitating the elimination thereof for the subsequent stages, and by the poor yields of final di-n-propyl acetic acid.

Consequently, it is essential to find a process for the preparation of di-n-propyl acetic acid with has the following qualities:
— simplicity as regards procedure,
— shorter overall time,
— higher yields,
— lowest possible cost of production, so that it may be validly employed on the industrial scale.

In accordance with the present invention, it has now been discovered that it is possible to obtain di-n-propyl acetic acid and its alkali and alkaline earth metal salts by such a process which can be used industrially, starting with a cyanacetic ester.

Thus, in accordance with the process of the invention, di-n-propyl acetic acid and its alkali and alkaline earth metal salts are prepared by reacting, in a single stage and in n-propanol medium a cyanacetic acid ester of the general formula:

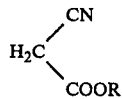

II in which R represents an alkyl radical having from 1 to 4 carbon atoms, preferably methyl or ethyl, with n-propyl bromide or iodide in the presence of sodium n-propylate, then by saponifying the crude ester thus obtained and by acidifying the salt thus formed with a strong acid, such as for example hydrochloric acid, in order to obtain the crude di-n-propyl cyanacetic acid, which is decarboxylated by heating to a temperature between 140° C. and 190° C., which provides the di-n-propyl acetonitrile. The di-n-propyl acetonitrile thus obtained is then hydrolysed by means of an aqueous solution of 75 to 80% sulphuric acid at a temperature from 80° C. to 140° C. to obtain the crude di-n-propyl acetamide, which is hydrolysed by means of an aqueous solution of 75 to 80% sulphuric acid at a temperature from 40° C. to 80° C. in the presence of sodium nitrite, to give the di-n-propyl acetic acid, which is reacted, if so desired, with an alkali metal hydroxide or alkaline earth metal oxide to provide the corresponding salt.

The starting products of formula II are either known products, having been published in J. Am. Chem. Soc., 43, 205–208 (1921), or products which may be prepared by known methods.

As regards the alkylation phase of the cyanacetic ester by means of a halide, the mode of use of the reactants will be such that the sodium n-propylate in n-propanol medium will be added, at a temperature between 45° C. and 55° C., to a reaction medium comprising the cyanacetic ester and the n-propyl halide. The alkylation reaction is then carried out under reflux for 3 hours.

Saponification of the crude di-n-propyl cyanacetic ester will be advantageously effected at a temperature between 60° and 70° C. for 3 hours by means of a 10 to 20% by weight sodium or potassium hydroxide solution in the proportion of 1.25 to 2 mols of hydroxide/mol of ester.

Subsequent acidification can be effected, for example, with a 36% by weight hydrochloric acid solution at a temperature slightly lower than 40° C.

According to a variation of the process, the saponification phase can take place in the presence of a quaternary ammonium salt, such as for example trimethyl cetyl ammonium bromide, benzyl trimethyl ammonium chloride or lauryl trimethyl ammonium bromide.

The concentration of quaternary ammonium salt may vary from 0.005 mol to 0.1 mol/mol of di-n-propyl cyanacetic ester.

The saponification temperature and also the time necessary for this operation will vary as a function of the quantity of quaternary ammonium salt used.

For a quaternary ammonium salt concentration of 0.1 mol/mol of ester, the saponification will take place over a period of 3 hours at 30° C., and for a concentration of 0.005 mol/mol of ester, the operation will be effected in one hour at 60°–65° C.

As regards the decarboxylation phase, this will be effected on the crude di-n-propyl cyanacetic acid at a temperature between 140° and 190° C., preferably between 175° and 190° C.

According to a variant of this last operation, decarboxylation of the di-n-propyl cyanacetic acid is carried out continuously. After having brought the acid in question to a temperature of 185°–190° C. and initiated the decarboxylation reaction, there is effected a continuous transfer of di-n-propyl cyanacetic acid with simultaneous elimination of the liberated carbon dioxide gas and of the di-n-propyl acetonitrile formed.

As regards the hydrolysis of the di-n-propyl acetonitrile, this will advantageously be carried out by means of 80% by weight sulphuric acid in the proportion of 3 to 5 g of dilute acid/g of nitrile, for example, 3.75 g of dilute acid/g of nitrile over a period of 90 minutes at 80°–85° C. and adding to the resulting amide an aqueous solution of sodium nitrite in the proportion of 1.4 mol of nitrite/mol of di-n-propyl acetonitrile, the reaction taking place for 2 hours at 40°–50° C. It will also be just as advantageous to use a 75% by weight sulphuric acid aqueous solution in the proportion of 1.7 g of dilute acid/g of nitrile for 30 minutes at 140° C., to obtain the intermediate di-n-propyl acetamide, which is hydrolysed in the same sulphuric acid medium in the presence of sodium nitrite in the proportion of 1.4 to 1.5 mol of nitrite/mol of di-n-propyl acetonitrile for one hour at 50°–60° C.

It will be preferable to use an aqueous solution of sodium nitrite rather than the product in powder form, which presents two disadvantages industrially: first of all, a problem as regards safety on account of the liberation of nitrous vapours and then a problem of strong local concentrations of nitrite, which are favourable to the formation of nitrous vapours and to an unsatisfactory temperature control.

Consequently, the process of the invention avoids these inconveniences, characteristic of the respective processes of SAREL and collaborators and TSAI and collaborators, which introduce the sodium nitrite in powder form into the hydrolysis medium.

The alkali metal salts of the di-n-propyl acetic acid will be prepared by adding a solution of the appropriate alkali metal hydroxide to a solution of di-n-propyl acetic acid. The alkaline earth metal salts will be prepared by reacting di-n-propyl acetic acid with an oxide of the appropriate alkaline earth metal as exemplified in U.S. Pat. No. 3,814,812.

The process of the invention presents undeniable advantages as compared with the processes suggested by the prior art. In the first place, the process of the invention offers the possibility of obtaining high yields of di-n-propyl acetic acid and of its alkali and alkaline earth metal salts in pure form, the yields being at least 76% relatively to the initial cyanacetic ester, whereas using the process according to the prior art, it has not been possible to obtain yields higher than 40% relatively to the same initial ester.

Moreover, the process of the invention is decidedly more simple than those of SAREL and collaborators and TSAI and collaborators mentioned above. For example, the process of the invention permits the alkylation of the cyanacetic ester to be effected in a single phase, comprising one single use of the n-propyl halide and of the alkali metal n-propylate, while TSAI and collaborators introduce the alcoholate and the halide in three different phases for each product.

The durations of the alkylation and saponification phases are also considerable in the case of the known processes: at least 8 hours for the alkylation phase according to TSAI and collaborators and 26 hours for the saponification phase according to these same authors.

As against this, the process of the invention permits the corresponding phases of alkylation and saponification to be effected much more quickly than by means of the known processes.

As regards the saponification phase, the time necessary for this operation will be advantageously reduced in the presence of a quaternary ammonium salt, for example, trimethyl cetyl ammonium bromide. This quaternary ammonium salt offers in addition the advantage of reducing the danger of hydrolysis of the nitrile function of the di-n-propyl cyanacetic ester.

Furthermore, the decarboxylation phase of the known processes necessitates, as well as a raising of the temperature, the addition of a supplementary product, either potassium hydroxide or copper powder.

According to the invention, the decarboxylation phase is carried out simply by heating the di-n-propyl cyanacetic acid.

Finally, the hydrolysis of the di-n-propyl acetonitrile is carried out in two stages according to SAREL and collaborators, necessitating two different concentrations of sulphuric acid and the intermediate separation of the di-n-propyl acetamide, which can be avoided with the process of the invention.

Another disadvantage presented by the processes suggested by the prior art, and more especially by the alkylation phases envisaged in these processes, lies in the recovery of the solvent, the reactants which have not reacted and the by-products formed during the reaction.

This operation of recovery, which is fairly difficult when using sodium ethylate/ethanol or sodium methylate/methanol, is found to be facilitated by using the sodium n-propylate/n-propanol pair, which offers a greater possibility of separation by distillation of the unreacted n-propyl halide, of the ether formed during the reaction and of the alcohol liberated by transesterification of the cyanacetic ester by the n-propanol.

All these disadvantages which are presented by the processes suggested in the prior art increase the quantity of material which is to be used, the labour force and the energy consumption, causing a concurrent increase in the cost price.

Among the disadvantages presented by the known processes, the presence of harmful impurities at the different stages is certainly not the least negligible.

These impurities, which are present at each phase during the process, singularly complicate the successful performance of the said process. It thus becomes necessary for them to be eliminated at each stage, which considerably increases the intermediate handling operations which are always costly on the industrial scale.

For example, the processes suggested by the prior art envisage the elimination of the monoalkylated product after the alkylation phase, this being done by means of 10% potassium hydroxide.

The alkylation phase envisaged within the scope of the process according to the invention enables the intermediate purification of the di-n-propyl cyanacetic ester to be avoided, which ester can be used in crude form.

It has in fact been observed that, since the use of the alkylation reactants, according to the invention, is based essentially on the introduction of sodium-n-propylate/n-propanol into a medium formed by the ester of formula II and n-propyl halide, the particular advantage is obtained of avoiding to a maximum extent the formation of monopropyl cyanacetic ester, which is much more considerable when the n-propyl halide is added to the mixture of cyanacetic ester/sodium n-propylate. This monopropyl cyanacetic ester will, in fact, subsequently lead to the formation of valeronitrile, and then to valeric acid, which is particularly troublesome on account of its disgusting odour. It is thus imperative that this valeric acid be eliminated from the final di-n-propyl acetic acid.

The use of the alkylation reactants according to the invention permits a very substantial reduction in the intermediate content of valeronitrile in the di-n-propyl acetonitrile, this content passing from about 3.6% according to the known processes to only 0.3% in accordance with the process of the invention.

Furthermore, the use of sodium n-propylate/n-propanol in accordance with the invention has been found to be much more advantageous than the use of sodium ethylate/ethanol or of sodium methylate/methanol, as proposed by the processes of the prior art.

It has in fact been established that the content of monopropyl cyanacetic ester in the crude di-n-propyl cyanacetic ester, which subsequently leads to the formation of valeronitrile and valeric acid, increases and may even vary from 2 to 5% if the reflux temperature of the reaction medium is too low at the time of the alkylation phase, which is the case with methanol and ethanol.

Moreover, it has been found that the use of the sodium ethylate/ethanol pair can give rise to the formation of a not inconsiderable quantity of ethyl-n-propyl-cyanacetic ester at the time of the alkylation phase, in an amount of about 1%.

Furthermore, the saponification of the crude di-n-propyl cyanacetic ester in accordance with the processes suggested by the prior art, that is to say, by means of 35% potassium hydroxide over a period of 16 to 26 hours, gives a crude di-n-propyl cyanacetic acid which contains from 18 to 34% of an impurity, which seems to be a di-n-propyl formamido-acetic ester. This latter product does not lead to the intermediate di-n-propyl acetonitrile, but to di-n-propyl acetamide. As the di-n-propyl acetonitrile, obtained following the decarboxylation of the corresponding cyanacetic acid, is recovered directly by distillation in accordance with the invention, the di-n-propyl acetamide in question is lost, which reduces the yield of nitrile and at the same time the yield of final di-n-propyl acetic acid.

Again, the process of the invention avoids this disadvantage.

It is clear from all the results set out above that the process of the invention represents an undoubted advantage by comparison with the processes suggested by the prior art.

The process of the invention is likewise found to be better than the previously mentioned conventional process. For example, each stage of the process of the invention involves one single use of the reactants, which is not the case with the conventional process in question. Secondly, the process of the invention only causes the formation of a minimum of impurities which are in any case easily eliminated.

Finally, the process of the invention is particularly economical: the cost of production of the di-n-propyl acetic acid and of its alkali and alkaline earth metal salts as prepared by the process of the invention is 2 to 2½ times less than in accordance with the conventional process.

The following Examples which have no limiting character, illustrate the process of the invention:

EXAMPLE 1

Preparation of di-n-propyl acetic acid (a) Di-n-propyl cyanacetic acid

First of all, a solution of sodium n-propylate was prepared from 7.42 g (0.322 mol) of sodium and 180 ml of anhydrous n-propanol, by heating under gentle reflux until all the sodium had been dissolved.

Into a 500 ml spherical flask, equipped with a dropping funnel, a mechanical stirrer, a thermometer and a condenser above which was a calcium chloride trap were introduced 16.95 g (0.141 mol) of ethyl cyanacetate and 40.69 g (0.33 mol) of n-propyl bromide. This mixture was heated to 45° C. and then, slowly and while stirring, the previously prepared sodium n-propylate solution was added thereto, the temperature of the reaction medium being maintained at 50°–55° C. by gentle external cooling. At the end of the operation of introduction, the temperature of the mixture was brought to reflux in 30 minutes and maintained under reflux for 3 hours. The n-propanol was then distilled and the distillation stopped when the temperature of the residual mass had reached 115° C.

The crude ester obtained in this manner was then treated with a solution of 7.5 g of sodium hydroxide in flake form in 67.5 ml of water. The mixture was placed in a 250 ml spherical flask equipped with a condenser, and then the reaction medium was slowly brought to 60°–70° C. This temperature was maintained for 3 hours, whereafter the medium was cooled to about 50° C. and the formed ethanol and the remainder of the n-propanol were eliminated under a pressure of 70 mm. Hg. The solution thus obtained was cooled to 20° C. and it was acidified, while being stirred, by adding 26.25 g of 36% by weight hydrochloric acid. During this operation, the temperature of the reaction medium was kept below 40° C. by cooling. Stirring was continued for 30 minutes and then the medium was left standing for 30 minutes. The oily layer of di-n-propyl cyanacetic acid was decanted and the aqueous phase was extracted with 35 ml of toluene. The toluene extract was added to the decanted di-n-propyl cyanacetic acid and then the toluene solution was washed, in a separation funnel, with a solution of 1.5 g of sodium chloride in 14 ml of water. The toluene phase was decanted and then the toluene was distilled under atmospheric pressure.

Using this procedure, 25 g of crude di-n-propyl cyanacetic acid were obtained.

(b) Di-n-propyl acetonitrile

Into a 100 ml spherical flask fitted with a thermometer and a condenser were introduced 25 g of crude di-n-propyl cyanacetic acid, obtained by the method described above, and the mixture was heated on an oil bath.

Decarboxylation commenced at a temperature close to 140° C. The mixture was then brought to reflux temperature, that is to say, to about 160° C. and then to 190° C. in 2 hours. This temperature was maintained until termination of the release of gas, which required 2 hours. The di-n-propyl acetonitrile thus formed was then slowly distilled and the fraction passing over between 165° C. and 175° C. was collected. A second distillation was then carried out.

Using this procedure, 14.7 g of di-n-propyl acetonitrile were collected. B.P.: 170° C. Yield: 83%, with respect to the ethyl cyanacetate employed.

(c) Di-n-propyl acetic acid

Into a 100 ml spherical flask fitted with a mechanical stirrer, a dropping funnel, a nitrogen inlet, a thermometer and a condenser, were introduced 40 g of 80% by weight sulphuric acid.

By means of the funnel, there were then slowly added 8 g (0.064 mol) of di-n-propyl acetonitrile prepared by the above-described method. The mixture was heated to 80°–82° C. and was kept at this temperature for 2 hours. It was then cooled to 50°–52° C. and, while this temperature was maintained by gentle external cooling, a solution of 6.2 g (0.09 mol) of sodium nitrite in 10 ml of water was introduced under vigorous stirring and by means of the funnel. When the operation of introduction had been completed, the mixture was cooled to 20° C. under a gentle stream of nitrogen and 30 ml of water was added through the funnel. Stirring was maintained for 30 minutes and then the mixture was allowed to decant for 30 minutes into a separation funnel. The organic phase was separated and the aqueous phase was extracted with 10 ml of toluene. This toluenic phase was added to the crude di-n-propyl acetic acid obtained and the toluenic solution was extracted with a solution of 2.8 g of sodium hydroxide in 25 ml of water. After decantation, the toluenic phase was eliminated and the alkali aqueous phase acidified by adding 8 g of 36% by weight hydrochloric acid. After decantation, the organic phase was collected and the aqueous phase extracted with toluene. The two organic phases were combined and three successive washing operations with 8 ml of water carried out. The toluene was distilled at atmospheric pressure and a residue weighing 9 g, representing a yield of 97% of crude di-n-propyl acetic acid was obtained.

The purification of the crude acid thus obtained was then effected by reduced-pressure distillation at 105°–108° C./5 mm. Hg.

In this way, 8.55 g of pure di-n-propyl acetic acid were collected. Yield: 92.7%, relatively to the di-n-propyl acetonitrile introduced.

Other tests concerning the preparation of di-n-propyl acetic acid were carried out in accordance with the process of the above Example 1, but respecting the following operational conditions:

— hydrolysis of 125.2 g (1 mol) of di-n-propyl acetonitrile with 75% by weight aqueous sulphuric acid in the proportion of 1.7 g of dilute acid/g of di-n-propyl acetonitrile, — temperature of the hydrolysis of the di-n-propyl acetonitrile to non-isolated crude di-n-propyl acetamide: 140° C., — time for the hydrolysis of the di-n-propyl acetonitrile to non-isolated crude di-n-propyl acetamide: 30 minutes, — hydrolysis of the non-isolated crude di-n-propyl acetamide in the presence of 103.5 g (1.5 mols) of sodium nitrite, — hydrolysis temperature of the non-isolated crude di-n-propyl acetamide: 50°–60° C., — time for the hydrolysis of the non-isolated crude di-n-propyl acetamide: 60 minutes.

A first test yielded the pure di-n-propyl acetic acid with a yield of 93% and a second test with a yield of 96%, both being calculated on the basis of the nitrile used.

EXAMPLE 2

Preparation of sodium di-n-propyl acetate

First of all, the crude di-n-propyl acetic acid was prepared from 8 g of di-n-propyl acetonitrile by the method described in Example 1.

This acid was purified by drying the solution in toluene by azeotropic distillation of the water and the solution was cooled to 20° C. This solution contained 9 g (0.062 mol) of di-n-propyl acetic acid, determined by acidimetric titration.

A solution of sodium hydroxide in methanol was then prepared by dissolving 2.458 g (0.0614 mol) of sodium hydroxide in tablet form in 13 g of methanol, while keeping the mixture lukewarm by cooling, and then filtering.

Into a 100 ml spherical flask equipped with a mechanical stirrer, a thermometer, a dropping funnel and a condenser, containing the previously prepared solution of di-n-propyl acetic acid in toluene, was introduced, under vigorous stirring, the solution of sodium hydroxide in methanol so obtained. Stirring was continued for 30 minutes after completing the operation of addition, and then the reaction medium was decolorised with active carbon. The active carbon was then filtered, the filter was rinsed with a small amount of toluene and the methanol and the water formed by the neutralisation were distilled. The solution of sodium di-n-propyl acetate in toluene was cooled to 20° C. and it was kept at this temperature for 2 hours while being stirred. The crystals were filtered, washed with a small amount of acetone and then dried. In this way, 9.75 g of sodium di-n-propyl acetate were obtained, representing a yield of 91.8% with respect to the di-n-propyl acetonitrile used.

EXAMPLE 3

Preparation of di-n-propyl acetic acid (a) Di-n-propyl cyanacetic acid

First of all, a solution of sodium n-propylate was prepared from 50 g (2 at. g + 10%) of sodium and 804 g (1000 ml) of anhydrous n-propanol by heating at 50°–55° C. for 60–90 minutes.

Into a 2-liter spherical flask were introduced 99.1 g (1 mol) of methyl cyanacetate and 270.6 g (2.2 mols) of n-propyl bromide. The mass was brought to 45°–50° C. while being stirred and, at this temperature, the solution of sodium n-propylate in propanol was regularly introduced. This operation lasted from 60 to 75 minutes.

When the operation of introduction was completed, the mixture was brought under reflux for 3 hours. The n-propanol was then distilled until 120°–125° C. was reached in the residual mass. The crude ester obtained was then treated with 500 g of a 10% by weight sodium hydroxide aqueous solution and with 0.36 g of cetyl trimethyl ammonium bromide. The mixture was brought under reflux for 1 hour, it was cooled to about 50° C. and then the residual alcohols were eliminated under reduced pressure (50 to 100 mm. Hg.). The solution obtained was cooled and then acidified, without exceeding 40° C., by means of 175 g of 36% by weight hydrochloric acid. The mixture was kept thus for 30 minutes and then the di-n-propyl cyanacetic acid was decanted. The lower aqueous layer was extracted with 250 g of toluene. The two organic phases were combined, washed once with 100 g of purified water and the solvent was eliminated by distillation under reduced pressure so as to obtain 154.5 g of crude di-n-propyl cyanacetic acid.

(b) Di-n-propyl acetonitrile

The crude di-n-propyl cyanacetic acid obtained above was transferred into a 250 ml spherical flask and progressively brought under reflux, with elimination of the last traces of toluene by means of a Dean-Stark system until a mass temperature of 175°–180° C. was reached. Decarboxylation started at about 140° C. and the reaction was practically complete after 1 hour under reflux. The mixture was kept under reflux for a total time of 2 hours. The mass temperature reached 205°–210° C. in the first minutes of the refluxing operation and dropped down again and became stable in the region of 185° C. The mixture was then distilled at atmospheric pressure.

In this way, 102.5 g of di-n-propyl acetonitrile were collected. Yield of crude product: 82%, relatively to the methyl cyanacetate Yield of pure product: 80% According to a modified procedure, the di-n-propyl acetonitrile was prepared in the following manner:

Into a 50-liter enamelled vessel were introduced 30 kg of di-n-propyl cyanacetic acid. While stirring, the reaction medium was heated to reflux at 185°–190° C. and this temperature was maintained for 15 minutes. The di-n-propyl acetonitrile thereby formed was then distilled while 69.4 kg of di-n-propyl cyanacetic acid were introduced in a continuous manner. The speed of introduction was regulated as a function of the speed of distillation of the nitrile, while the temperature of the mass was maintained at 185°–190° C.

The operation of introduction lasted about 4½ hours, during which time 40.9 kg of crude di-n-propyl acetonitrile were collected. Distillation was continued by gradually raising the temperature of the mass to 206° C. and maintaining it at this level until the end of the operation. This operation lasted 6 hours, during which time 16.350 kg, and then again 8.980 kg of crude di-n-propyl acetonitrile were recovered. The apparatus was brought under reduced pressure (about 100 mm. Hg.) and a new fraction of 1.640 kg of di-n-propyl acetonitrile was recovered.

In this way, 67.87 kg of crude di-n-propyl acetonitrile were obtained.

(c) Di-n-propyl acetic acid

Into a spherical flask were introduced 469.5 g of an 80% by weight sulphuric acid aqueous solution. 125.2 g (1 mol) of di-n-propyl acetonitrile were then added in 15 minutes and the temperature was raised to 80° C. for 90 minutes to effect the hydrolysis into amide. The flask was cooled to 50° C. and 96.5 g (1.4 mol) of sodium nitrite in 146 g of water were introduced at this temperature and in 2 hours. The temperature of the reaction medium was kept at 40°–50° C. during this operation and then it was cooled to 15°–20° C.

The nitrous vapours were degasified by a stream of nitrogen and then hydrolysis was carried out with 330 g of purified water without exceeding +30° C. in the mass. The crude di-n-propyl acetic acid in the upper phase was decanted and the aqueous phase extracted with 140 g (160 ml) of toluene. The organic phases were combined and the acid was extracted in the form of a sodium salt by means of a solution of 44 g of sodium hydroxide in 250 g of purified water. While stirring, the whole was brought to about 60° C. for 15 minutes, the upper toluenic phase containing the impurities incapable of forming a salt were eliminated by decantation and then the aqueous phase of sodium di-n-propyl acetate was acidified by progressive addition, at room temperature, of 120 g of 36% by weight hydrochloric acid. The decidedly acid pH value was checked, the supernatant di-n-propyl acetic acid was decanted and the aqueous phase was extracted with 140 g of toluene. The two organic phases were combined, they were washed to pH ≧ 4 with three fractions of purified water, each of 50 g, and the solution in toluene was dried by azeotropy. The crude di-n-propyl acetic acid thus obtained was then purified by distillation under reduced pressure at 105°–108° C./5 mm. Hg.

In this way, pure di-n-propyl acetic acid was obtained with a yield of 92.6%.

EXAMPLE 4

Preparation of sodium di-n-propyl acetate 290 g (about 1 mol of acid) of a solution in toluene of crude di-n-propyl acetic acid obtained in Example 3 were placed in a 1000 ml Erlenmeyer flask. The dilution was brought to about 28% by weight by addition of toluene and then a 16% by weight solution of sodium hydroxide in methanol was progressively introduced, while stirring in the proportion of 39.2 g of sodium hydroxide to 210 g of methanol. The reaction mixture was treated at room temperature for 30 minutes with 7.2 g of active carbon. The mixture was filtered over sintered glass and rinsed with 40 g of toluene and then with 20 g of methanol. The filtrates were combined in a 1000 ml spherical flask and the methanol and the water were eliminated by distillation at atmospheric pressure until a temperature of 108°–110° C. was reached at the top of the column, while 140 g of toluene were progressively added so as to avoid excessive thickening.

In this way, a distillate weighing about 670 g was obtained. This was cooled to room temperature by means of a water bath and was suction-filtered after being kept for 2 hours at +15°–20° C., under a nitrogen atmosphere, and the product obtained was successively washed with 15 g of iced acetone and then with 15 g of iced acetone containing 0.28 g of di-n-propyl acetic acid. Drying to constant weight was effected in a vacuum oven and under a gentle stream of nitrogen at 50° C.

In this manner, sodium di-n-propyl acetate was obtained with a yield of 99% relatively to the di-n-propyl acetic acid introduced.

Other tests carried out in identical manner enabled sodium di-n-propyl acetate to be obtained with yields of respectively 99.7% and 99.8%, calculated on the di-n-propyl acetic acid.

We claim:

1. Process for the preparation of di-n-propyl acetic acid of formula:

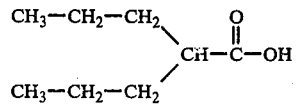

and its non-toxic alkali and alkaline earth metal salts whereby, in a single stage, sodium n-propylate in n-propanol medium is added to a reaction medium formed of a cyanacetic ester of general formula:

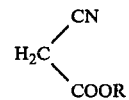

in which R represents an alkyl radical having from 1 to 4 carbon atoms, and n-propyl bromide or iodide, the alkylation reaction taking place under reflux, the crude ester obtained is saponified with a 10 to 20% solution of sodium or potassium hydroxide, the salt thus obtained is acidified with a strong acid, to give the crude di-n-propyl cyanacetic acid, which is decarboxylated by heating at a temperature between 140° and 190° C., to provide the di-n-propyl acetonitrile, the di-n-propyl acetonitrile obtained is hydrolysed by means of an aqueous solution of 75 to 80% sulphuric acid at a temperature of 80–140° C. to give the crude di-n-propyl acetamide, which is hydrolysed by means of an aqueous solution of 75–80% sulphuric acid at a temperature of 40°–80° C. in the presence of sodium nitrite, to provide di-n-propyl acetic acid, which is caused to react, optionally, with an alkali metal hydroxide or alkaline earth metal oxide in order to obtain the corresponding salt.

2. Process according to claim 1, whereby the cyanacetic ester is methyl or ethyl cyanacetate.

3. Process according to claim 1, whereby the addition of sodium n-propylate takes place at the temperature of 45°–55° C.

4. Process according to claim 1, whereby the saponification takes place at a temperature between 30° and 70° C.

5. Process according to claim 1, whereby the saponification is effected in the proportion of 1.25 to 2 mols of potassium or sodium hydroxide/mol of crude ester.

6. Process according to claim 1, whereby the saponification is carried out in the presence of a quaternary ammonium salt.

7. Process according to claim 6, whereby the quaternary ammonium salt is trimethyl cetylammonium bromide.

8. Process according to claim 6, whereby the saponification is carried out in the presence of 0.005 to 0.1 mol of quaternary ammonium salt mol of crude ester.

9. Process according to claim 1, whereby the acidification is effected by means of 36% hydrochloric acid at a temperature not exceeding 40° C.

10. Process according to claim 1, whereby the decarboxylation takes place at a temperature between 175° C. and 190° C.

11. Process according to claim 1, whereby the decarboxylation operation is effected in a continuous manner while simultaneously eliminating the formed di-n-propyl acetonitrile.

12. Process according to claim 1, whereby the di-n-propyl acetonitrile is hydrolysed by means of 80% aqueous sulphuric acid, in the proportion of 3 to 5 g of dilute acid/g of nitrile, at a temperature of 80°–85° C., and then the crude di-n-propyl acetamide thus obtained is hydrolysed in the same aqueous sulphuric acid medium in the presence of 1.4 mol of sodium nitrite/mol of nitrile, at a temperature of 40°–50° C.

13. Process according to claim 12 whereby the di-n-propyl acetonitrile is hydrolysed by means of 80% aqueous sulphuric acid in the proportion of 3.75 g of dilute acid/g of nitrile.

14. Process according to claim 1, whereby the di-n-propyl acetonitrile is hydrolysed by means of 75% aqueous sulphuric acid in the proportion of 1.7 g of dilute acid/g of nitrile at the temperature of 140° C. and then the crude di-n-propyl acetamide thus obtained is hydrolysed in the same aqueous sulphuric acid medium in the presence of 1.4 to 1.5 mol of sodium nitrite/mol of nitrile at a temperature of 50°–60° C.

15. Process according to claim 1, whereby the non-toxic alkali metal salts are the lithium, sodium or potassium salts.

16. Process according to claim 1, whereby the non-toxic alkaline earth metal salts are the magnesium and calcium salts.

* * * * *